United States Patent [19]

Leston

[11] 3,992,455
[45] Nov. 16, 1976

[54] PREPARATION OF 5-SEC-ALKYL-M-CRESOL

[75] Inventor: Gerd Leston, Scott Township, Pa.

[73] Assignee: Koppers Company, Inc., Pittsburgh, Pa.

[22] Filed: Oct. 1, 1973

[21] Appl. No.: 402,160

[52] U.S. Cl. .................. 260/619 R; 260/619 D; 260/621 R; 260/624 C; 260/620; 260/626 T; 424/366; 424/286
[51] Int. Cl.$^2$ .................. C07C 37/14; C07C 39/06
[58] Field of Search ......... 260/626 T, 626 R, 624 E, 260/621 E, 620, 626, 624 C, 619 D, 624 R, 619 R

[56] References Cited
UNITED STATES PATENTS

| | | | |
|---|---|---|---|
| 1,886,311 | 11/1932 | Skraup et al. | 260/626 T |
| 2,054,270 | 9/1936 | Schoeller et al. | 260/619 D |
| 2,064,885 | 12/1936 | Carpenter | 260/626 T |
| 2,286,953 | 6/1942 | Carpenter | 260/626 T |
| 2,898,322 | 8/1959 | Shepard et al. | 260/626 |
| 3,014,079 | 12/1961 | Olin | 260/624 E |
| 3,290,389 | 12/1966 | Huhn | 260/626 R |
| 3,360,573 | 12/1967 | Walts et al. | 260/624 C |
| 3,655,778 | 4/1972 | Kohn | 260/619 D |
| 3,655,780 | 4/1972 | Kohn et al. | 260/621 E |

FOREIGN PATENTS OR APPLICATIONS

| | | | |
|---|---|---|---|
| 298,364 | 9/1963 | Netherlands | 260/621 |

OTHER PUBLICATIONS

Babakhanov et al., "Chem. Abs.," vol. 69 (1968) 106078w.

Hoechst, "Chem. Abs.," vol. 62 (1965) 6635d.

Keder et al., "Chem. Abs.," vol. 64 (1966) 2795c.

Primary Examiner—Bernard Helfin
Assistant Examiner—W. B. Lone
Attorney, Agent, or Firm—Herbert J. Zeh, Jr.; Oscar B. Brumback

[57] ABSTRACT

This disclosure is directed to a method for preparing 5-sec-alkyl-m-cresol in high concentrations and yields comprising alkylating m-cresol with an alkene over a solid catalyst selected from finely divided silica alumina clays and finely divided molecular sieves and then isomerizing the alkylated m-cresol product over the same catalyst for at least two hours at temperatures of at least about 250° C. The ratio of alkene to m-cresol is from about 0.5:1.0 to about 1.0:1.0. The resulting isomerized alkylated m-cresol contains a ratio of 5-alkyl-m-cresol to 6-alkyl-m-cresol of at least 2.5:1 and a ratio of 5-alkyl-m-cresol to 4-alkyl-m-cresol of at least 3.0:1.0. The desired 5-alkyl-m-cresol may be obtained from the isomerized alkylated-m-cresol reaction product by fractional distillation. The undesired alkylated-m-cresol isomers and unreacted m-cresol may be recycled into the alkylation and/or isomerization step. The method is particularly useful for preparing 5-isopropyl-m-cresol(m-thymol).

31 Claims, No Drawings

PREPARATION OF 5-SEC-ALKYL-M-CRESOL

BACKGROUND OF THE INVENTION

This invention is directed to an improved process for preparing 5-sec-alkyl-m-cresol. The process of this invention yields 5-sec-alkyl-m-cresol in higher yields and at a more economic cost than the present methods. The method comprises alkylating m-cresol with an alkene in the presence of a catalyst. The alkylated m-cresol mixture is then isomerized over the same catalyst to give a reaction mixture having a high concentration of 5-sec-alkyl-m-cresol and low concentrations of the other alkylated-m-cresols. The 5-sec-alkyl-m-cresol is recovered from the reaction product by fractional distillation and the other alkylated-m-cresols may be recycled.

This invention is particularly directed to an improved process for preparing 5-isopropyl-m-cresol (m-thymol). The invention yields m-thymol in higher yields and at a more economic cost than the present methods. The method comprises alkylating-m-cresol with propylene in the presence of a catalyst. The isoproplated m-cresol mixture is then isomerized over the same catalyst to give a reaction mixture having a high concentration of m-thymol and low concentrations of the other thymol isomers. The m-thymol is recovered by fractional distillation.

This invention is also directed to the composition of matter of 5-cyclohexyl-m-cresol and 5-α-methylbenzyl-m-cresol.

The compound 5-isopropyl-m-cresol is an extremely useful intermediate for preparing insecticides. It was postulated at a symposium on "Carbamate Insecticides" at the 148th ACS meeting in the fall of 1964 that the order of insecticidal activity of alkyl phenyl N-methyl carbamate was m-alkyl>> o-alkyl or p-alkyl, sec-alkyl>tert-alkyl>>n-alkyl and 4-carbon side chain> 3 or 5 carbon>>fewer or more carbons. Therefore the N-methyl carbamate of 5-isopropyl-m-cresol would be a very effective insecticide. In fact, the N-methylcarbamate of this compound has been patented for this use. See Jaeger and Peissker, German Pat. No. 1,147,438. In addition, the 5-isopropyl-m-cresol and other 5-sec-alkyl-m-cresols are valuable intermediates for preparing other compounds. It should be noted that 5-isopropyl-m-cresol is commonly referred to in the literature by several other names. In addition to 5-isopropyl-m-cresol the compound has been referred to as 3-isopropyl-5-methylphenol, symmethrical thymol (sym-thymol), 5-thymol, or m-thymol. These terms have been and may be used interchangeably for referring to the subject compound.

Although m-thymol and other 5-sec-alkyl-m-cresols are very useful compounds, they have not heretofore found wide commercial application. The main reason for this lack of commercialization is that before the invention herein there was no efficient and economical method for preparing 5-sec-alkyl-m-cresol particularly m-thymol. The process of the present invention is the best process considering ease of operation, cost of raw materials, disposal of by-products, recycling of isomers and unreacted starting materials and prevention of the formation of polyalkylated-m-cresols.

The compound 5-isopropyl-m-cresol has been known for many years. It was first synthesized by E. Knoevenagel in 1894 under the same symmetrical carvacrol. Knoevenagel brominated m-camphor forming the unstable dibromide which began to lose hydrogen bromide at room temperature. On heating, all the bromine was removed as HBr leaving s-carvacrol. The first indication that m-thymol was formed in the condensation of propylene with m-cresol over sulfuric acid was reported by Howard and Blagden in British Pat. No. 214,866, but the compound was not characterized. The reaction of m-cresol with isopropyl chloride using aluminum chloride as the catalyst is the subject of U.S. Pat. No. 2,064,885. According to the patent, thymol is the major product below −10° C. with a little m-thymol present. The latter is obtained almost pure if the condensation is performed at 30°–60° C.

Chichibabin studied the thymol isomers in greater detail Ann. de Chemie, 17,317 (1942) and gave the following physical constants:

| Isomer | Boiling Point | Melting Point |
|---|---|---|
| 2 - (vic) | 228.5°/760 mm. | 69° |
| Thymol (6-) | 231.8°/758 mm. | 50.5° |
| 5-(sym) | 241° | 51.0° |
| 4-(p-) | 245–6° | 114° |

He performed the condensations of m-cresol with isopropyl alcohol with both phosphoric and sulfuric acid catalysts, and the condensation of m-cresol with isopropyl chloride with an aluminum chloride catalyst. His work showed that the meta-isomer was the major product at elevated temperatures. In addition he postulated that the 5-isomer was the most stable isomer. Chichibabin expressed surprise that Smith, J. Am. Chem. Soc. 55,849, (1933), did not find m-thymol in the aluminum chloride-catalyzed isomerization of m-cresyl isopropyl ether. However, Niederl et. al; J. Am. Chem. Soc. 53,1928 (1931) and Sowa, et al, J. Am. Chem. Soc. 54,2019 (1932) also failed to isolate the symmetrical isomer of thymol.

Carpenter and Easter, J. Org. Chem. 20,401 (1955), studied the preparation of all isopropyl cresols and gave the following physical constants:

| Isomer | M.P., ° C | Oxyacetic Acid M.P., ° C | p-Nitrobenzoate M.P., ° C |
|---|---|---|---|
| 2-Isopropyl-3-methyl phenol (vic-thymol) | 70–1 | 147.5–148.5 | 107.5–108.5 |
| 4-Isopropyl-3-methyl phenol (p-thymol) | 112–3 | 128–9 | 143–4 |
| 5-Isopropyl-3-methyl phenol (sym-thymol) | 50–50.5 | 87–8 | 87–8 |
| 6-Isopropyl-3-methyl phenol (thymol) | 51.5 | 150 | 70 |

They obtained the pure 5-thymol by alkylation of m-cresol and hydrolysis of its p-nitrobenzoate.

A review of the literature shows that the following methods have been used to prepare m-thymol:

1. Bromination of 3-methyl-5-isopropyl-2-cyclohexen-1-one and dehydrobromination (Knoevenagel, 1894).
2. Dehydrogenation of 3-methyl-5-isopropyl-2-cyclohexen-1-one (Horning 1945, 1949).
3. Sulfonation of m-cresol, condensation with propylene and hydrolysis of sulfuric acid (Howard, Blagden, 1924).
4. Condensation of isopropyl chloride with m-cresol in ethylene dichloride by molar quantities of aluminum chloride (Carpenter, 1936; Chichibabin 1942 and 1955).
5. Condensation of isopropyl ether with m-cresol over acid clay (Carpenter and Easter, 1955).
6. From 2,6-dimethyl-4-isopropylpyrylium perchlorate and NaOH in 14% yield (Balaban and Nenitzescu).
7. Hydrolysis of 5-methoxy-7-methylthionaphthene over Raney nickel followed by hydrolysis of the ether by pyridine hydrochloride (Demerseman 1963).
8. Reaction of m-cresol with propylene in the presence of $ZnBr_2$—$H_2O$—HBr (Kalav 1972).

It is obvious that only a few of the above processes are capable of commercial production. Moreover, those which are capable of being used commercially are not economically feasible. For example, route 4 above requires large amounts of aluminum chloride which has to be removed. Also, isopropyl chloride instead of the much cheaper propylene is used. Route 5 is a feasible process but uses the more expensive and potentially hazardous isopropyl ether.

There is very little information available on the preparation and use of the 5-sec-alkyl-m-cresols other than m-thymol. There are a few references which teach about 5-ethyl-m-cresol and 5-t-butyl-m-cresol. In addition there are several references which disclose 5-sec-butyl-m-cresol. For example see the following references: U.S. Pat. No. 2,898,322; Journal of Chromatography 23 120 (1966) and Journal of Chromatography 23 417, (1966). I have been unable to find any reference to the composition of matter or use of other 5-sec-alkyl-m-cresols. The compounds 5-cyclohexyl-m-cresol and 5-α-methylbenzyl-m-cresol are new compositions of matter.

Therefore, it is the object of this invention to provide a method for economically preparing 5-sec-alkyl-m-cresol particularly 5-isopropyl-m-cresol.

SUMMARY OF THE INVENTION

I have discovered an improved and economical process for preparing 5-sec-alykl-m-cresol particular 5-isopropyl-m-cresol in high concentrations and high yields. The method comprises alkylating m-cresol with an alkene over a certain finely divided catalysts to obtain a mixture of alkylated m-cresols. The mixture of sec-alkyl-m-cresols is then isomerized over the same catalyst at high temperatures to yield a product containing a major amount of m-sec-alkyl-m-cresol and minor amounts of the other isomeric sec-alkyl-m-cresols. The mixture also contains small amounts of dialkylated m-cresols and unreacted starting materials. The desired m-sec-alkyl-m-cresol is obtained by fractional distillation. The undesired products may be returned to the alkylation/isomerization reaction step.

The reaction of propylene with m-cresol to form isopropylated-m-cresols is not a novel reaction. However, the method of running the present reaction and the products obtained thereby are novel and unexpected in view of the prior art. The reaction of propylene with m-cresol to form thymol is disclosed in Skraup et al, U.S. Pat. No. 1,886,311. This patent also discloses that other isomers of thymol are formed. However, the patent teaches that only thymol is obtained in high yields. The patent does not identify the formation of m-thymol. According to Skraup, U.S. Pat. No. 1,886,311 no m-thymol is formed during the reaction of propylene with m-cresol. Thymol, vic-thymol, and p-thymol are formed but not m-thymol. In addition, Schollkopf et al, U.S. Pat. No. 1,876,435 is directed to the preparation of thymol by isomerization of the isomers of thymol. According to Schollkopf thymol may be prepared by isomerizing vic-thymol, p-thymol and the like over a catalyst at elevated temperatures. This patent teaches that almost complete conversion of the isopropylated derivatives of m-cresol into thymol may be obtained. This teaching is the exact opposite of the present invention. In addition, see the related patent of Schollkopf et al, U.S. Pat. No. 1,902,904, which teaches the formation of thymol by reacting m-cresol with propylene yielding substances. However, it should be noted that the process of my invention yields m-thymol as the major product of the isopropylation-isomerization of m-cresol with propylene over a solid catalyst.

The process of my invention comprises several steps. In the first step an alkene is reacted with m-cresol over a solid catalyst to form a reaction product which is a mixture of the various isomeric alkylated m-cresols and unreacted starting materials. The second step which is run immediately after the first step is an isomerization step. In fact the isomerization reaction occurs somewhat simultaneously with the alkylation step. In the isomerization step the isomeric forms of sec-alkyl-m-cresol are transalkylated so that the major constituent is 5-sec-alkyl-m-cresol. The resulting product after isomerization has a ratio of 5-sec-alkyl-m-cresol to 6-sec-alkyl-m-cresol which is greater than 2.5:1.0 and has a ratio of 5-sec-alkyl-m-cresol to 4-sec-alkyl-m-cresol or 2-sec-alkyl-m-cresol which is at least 3.0:1.0 and is usually greater than 20:1. The desired 5-sec-alkyl-m-cresol is recovered by fractionally distilling the isomerized product. The cuts from the fractional distillation may be returned to the alkylation/isomerization reaction or if they contain substantial amounts of the desired product they can be recycled into the fractional distillation step.

When preparing m-thymol according to my invention propylene is reacted with m-cresol over the solid catalyst to yield a mixture of the various isopropylated m-cresols. This mixture is then isomerized to yield a resulting product which has a ratio of m-thymol to thymol which is greater than 2.5:1.0 and which has a ratio of m-thymol to p-thymol or vic-thymol which is at least about 8.0:1.0 and is usually greater than 20:1. The desired m-thymol is recovered by fractional distillation.

As mentioned above, both the alkylation step and isomerization step are run in the presence of a solid catalyst. I have found that two types of catalysts are particularly effective. One type of catalyst is the silica-alumina clays. The silica-alumina clays are the clays which have silica as the major mineral and the second major mineral being alumina. The silica-alumina clay catalysts generally contain from 50-90% by weight silica measured as $SiO_2$ and from about 10-25% by weight alumina measured as $Al_2O_3$. It is also well known that most of the silica-alumina clay catalysts are acid activated. Another type of useful catalysts are the molecular sives. The molecular sieves which are sueful in my invention are the large pore diameter faujasite type which have been exchanged with multivalent cations or with hydrogen. Examples of the useful mol sieves are the type X and type Y zeolites. I have tried the mordenites mol sieves but they do not work. I have found that the rare earth exchange zeolite mole sieve catalysts are particularly effective. One of the most useful of this type is Linde's type Y molecular sieve. The catalysts should be finely divided and should pass through a Tyler Standard Sieve of 100 mesh preferably greater than 75% pass through a 352 mesh screen.

The catalyst is employed in concentrations of from about 1.0 to about 10.0% by weight based on the weight of m-cresol plus alkylated m-cresols. The initial alkylation reaction between the alkene and m-cresol proceeds very readily in the presence of very small amounts of catalyst. However, the isomerization reaction requires a substantial amount of catalyst. For example, catalyst concentrations of about 0.5% by weight will promote the alkylation reaction but isomerization proceeds slowly at this catalyst concentration. It is necessary to have catalyst concentrations of at least about 1% in order to have an effective rate of isomerication. The alkylation step may be run in the presence of less than 1% so long as at least 1% is present for the isomerization. However, catalysts concentrations greater than 10% do not tend to improve the isomerization rate. The preferred catalysts concentrations are from about 2 to about 7% by weight. It should be noted that the optimum catalyst concentration will be dependent on the individual catalyst used. The optimum concentration for each particular catalyst may easily be determined by routine experimentation.

After the isomerization step the catalyst is separated from the reaction mixture. The catalyst may be separated by any convenient technique. For example, the catalyst may be removed by filtrations, decantation or the like. The reaction mixture may be flashed from the catalyst. It is also within the scope of this invention to distill the product from the catalyst. After use the catalyst may be regenerated or discarded.

The temperature of alkylation and isomerization is another important factor. The temperature of the alkylation step is not as critical as the temperature of the isomerization step. The temperature of alkylation has to be sufficiently high in order to get a good rate of reaction. The minimum temperature required to effect alkylation at a good rate is about 100° C. The alkylation reaction should be initiated at a temperature greater than 100° C. However, higher alkylation temperatures give better initial yield of the desired m-isomer. Therefore, it is preferred to have alkylation temperatures of greater than 150° C. The isomerization temperature is considerably higher. In order to obtain a good isomerization the temperature should be between 250° and 400° C. I prefer temperatures between about 280° and 320° for isomerization. The alkylation reaction is exothermic. Advantage may be taken of this exothermicity to complete the alkylation near the desired isomerization temperature of 250° or higher.

Another important variable is the molar ratio of alkene to m-cresol. This ratio should be no greater than one mole of alkene per mole of m-cresol. Preferably the mole ratio of alkene to m-cresol should be from about 0.5:1.0 to about 0.9:1.0. At these lower ratios the concentration of 5-sec-alykl-m-cresol is lower than the concentration obtained at high molar ratios greater than 1.0:1.0. However, the molar ratios should be kept within the described range in order to avoid contamination of the 5-isomer with other components. When the molar ratios are 1.0:1.0 or higher there is a greater tendency to form di-alkylated and other unknown reaction products which are difficult to separate from the desired product. The unreacted m-cresol is not lost but recovered during the distillation step and reused.

Another variable which affects the reaction is time. Generally the alkylation step is completed within about 2 to 3 hours. The alkylation reaction goes very readily and seldom will require greater than 3 hours. The isomerization step generally requires a longer period. The transalkylation step generally takes from about 2 to 12 hours. Periods of less than 2 hours do not yield the desired ratio of the 5-isomer to the 6-isomer, 5-isomer to 2-isomer, and 5-isomer to 4-isomer. In addition, periods much greater than about 12 hours do not favorably increase these ratios. Therefore, the isomerization should be run for about 2–12 hours. The overall reaction period is then from about 4 to 15 hours. The optimum isomerization time is dependent on such factors as the amount and type of catalyst employed and can be determined by routine experimentation.

At the end of the alkylation step the reaction mixture contains a major amount of the 6-isomer (thymol). In fact the ratio of 6-isomer to the preferred 5-isomer is usually around 1:1 or higher. The ratio of 5-isomer to 4-isomer is also unfavorable and may be from about 6:1 to about 1:6. The reaction product also contains substantial portions of the other alkylated m-cresols and multiple alkylated addition products. However, at the end of the isomerization step the reaction mixture contains a high concentration of the 5-isomer. After isomerization the ratio of the 5-isomer, to the 6-isomer is at least 2.5:1 and often 5:1 or greater. In addition, the ratio of the 5-isomer to the 4-isomer is at least 3:1 and usually as high as 20:1 or greater. Moreover, the concentration of the other isomers and the amount of multiple alkylated compounds is greatly reduced.

After alkylation and isomerization the 5-isomer may be recovered from the reaction mixture by any convenient method. The most practical and preferred method is fractional distillation. This distillation must be performed very carefully in order to assure a product of desired purity. This is especially true for m-thymol. In this distilation almost all of the thymol must be removed from the product so that more allowance can be made for the 4-isomer (p-thymol) which boils just above the desired m-thymol as well as other close boiling components particularly the dipropylated m-cresols. Thus high reflux ratios are required, especially going into the plateau of the m-thymol and again somewhere during the plateau until the end of the plateau to minimize contamination with thymol and p-thymol. The thymol/m-thymol distillation intermediates and m-thymol/p-thymol disillation intermediates which contain substantial amounts of m-thymol are preferably recycled to distillation. The other undesirable by-products and along with recovered m-cresol can be recycled to alkylation and/or isomerization to raise the utlimate yield.

When recycling, the recycled m-cresol and alkylated m-cresol along with fresh m-cresol are introduced into the reaction along with sufficient catalyst so that it corresponds to from 0.5 to 10% of the weight of all the cresol, alkylated and unalkylated, but figured as unalkylated cresol. Thus, if 0.3 moles m-cresol where recycled and 0.5 moles of alkylated m-cresols were recycled along with 0.2 moles fresh m-cresol the total m-cresols present are one mole and from 0.54 to 10.8 grams of catalyst would be used. The amount of alkene to be added would be adjusted so that a ratio of alkene to m-cresol would be from about 0.5:1.0 to about 0.9:1.0.

It is also within the scope of this invention to simultaneously produce thymol and m-thymol. The m-cresol is first alkylated in accordance with the procedure described herein. Then the thymol is recovered by fractional distillation. The undesirable fractions and the residue from the fractional distillation are combined and subject to an isomerization process in accordance with the procedure described herein. The m-thymol is then recovered according to the present invention. Additional thymol may also be recovered after the isomerization step.

I have performed numerous experiments demonstrating my invention. The following examples are illustrative of the invention but should not be construed to limit the same:

EXAMPLE 1

Five moles of m-cresol (98% purity) and 5% by weight Filtrol 13, (an acid activated silica alumina clay) based on the m-cresol were charged to a reactor capable of pressure greater than 200 psig and high temperatures. The mixture of catalyst and m-cresol was agitated and heated. At about 150° C propylene was added until five moles had been introduced and reacted. The reaction product was then isomerized for about eight hours at 280° C. The reaction product was analyzed at the end of the propylene reaction and at the end of the 8 hour isomerization step. The reaction product was then separated from the catalyst and fractionally distilled at 50 mm and 19:1 reflux ratio. The details of this fractionation are shown in Table 2 below. As can be seen from this Table, fractions containing the m-thymol in 94–96% purities were isolated.

All distillation fractions containing less than 84% m-thymol were combined and analyzed with the results shown in Table 1. This combined material was then isomerized in the presence of 5% fresh Filtrol 13 for 11 hours at 280° C and gave the mixture shown in Table 1. The results shown in Table 1 and 2 illustrate that m-thymol can be isolated in high purity by fractional distillation and that the other isomers as well as di-isopropylated m-cresols could be isomerized and transalkylated to give a high concentration of the desired m-thymol.

TABLE 1

5-Isopropyl-m-Cresol by Isopropylation of m-Cresol

| | 1[1] | 7[2] | -Composite[3] | -Recycle Product[4] |
|---|---|---|---|---|
| | GC Analyses[5] Area Percent | | | |
| Unknowns | 1.5 | 1.0 | 0.1 | 1.5 |
| m-Cresol | 12.9 | 9.8 | 20.5 | 19.3 |
| Unknowns | 0.6 | 3.9 | 7.6 | 10.8 |
| Thymol | 29.0 | 19.2 | 41.9 | 18.1 |
| 5-Isopropyl-m-cresol | 12.1 | 46.9 | 3.2 | 34.0 |
| 4-Isopropyl-m-cresol | 9.3 | 2.1 | 1.7 | 2.0 |
| Unknowns | 4.8 | 4.2 | 5.5 | 6.5 |
| 4,6-Di-isopyl-m-cresol | 23.4 | 7.2 | 11.6 | 3.6 |
| Unknowns | 6.4 | 5.7 | 7.9 | 4.1 |

[1] End of propylene addition sample.
[2] End of eight-hour isomerizations sample, Distillation of this material is shown in Table 2.
[3] Composite of distillation fractions (Table 2) containing less than 84% 5-Isomer, Cut-A through -6, and -14 through -17.
[4] Product of 11 hr. isomerization of composite.
[5] 27 ft. Apiezon L Bentone 34 column No. 234, 170°, 81–86 ml.He./min. 50 psig, F&M model 500, 0.005 ml. sample injection (used herein unless otherwise stated).

TABLE 2

5-Isopropyl-m-Cresol by Isopropylation of m-Cresol

| Sample Cut - | -A | 1 | 2 | 3 | 4 | 5 | 6 | 7 | 8 | 9 | 10 | 11 | 12 |
|---|---|---|---|---|---|---|---|---|---|---|---|---|---|
| Distillation Temperatures (° C) | 123 | 125 | 129 | 145 | 148 | 154 | 158 | 159 | 159 | 159 | 159 | 159 | 160 |
| Sample Weight (g) | 3.8 | 49.5 | 9.9 | 14.8 | 51.2 | 41.1 | 34.2 | 26.5 | 38.4 | 16.2 | 48.4 | 32.5 | 37.0 |
| | GC ANALYSIS[1] AREA PERCENT | | | | | | | | | | | | |
| Unknowns | 7.0 | 0.2 | — | | | | | | | | | | |
| m-Cresol | 88.1 | 96.0 | 72.9 | 8.4 | 0.2 | 0.1 | trace | 0.1 | — | 0.1 | — | | |
| Unknowns | 1.7 | 3.8 | 20.9 | 53.7 | 18.4 | 2.5 | 1.1 | 0.5 | — | — | — | | |
| Thymol | 1.9 | 0.1 | 6.2 | 37.7 | 81.3 | 96.6 | 75.6 | 9.0 | 0.8 | 0.2 | 0.2 | 0.2 | — |
| 5-Isopropyl-m-Cresol | 1.1 | — | — | — | trace | 0.5 | 20.4 | 84.3 | 93.7 | 95.5 | 95.3 | 93.9 | 91.9 |
| 4-Isopropyl-m-Cresol | | | | 0.1 | — | 0.1 | 1.4 | 0.4 | 1.1 | 0.2 | 1.0 | 2.1 | 3.7 |
| Unknowns | | | | 0.1 | 0.2 | 0.4 | 1.2 | 5.6 | 4.4 | 3.8 | 3.5 | 3.7 | 3.7 |
| 4,6-Di-isopropyl-m-Cresol | | | | | | | | 0.1 | trace | — | — | — | — |
| Unknowns | | | | | | | | | | | | — | — |

| Sample Cut- | 13 | 14 | 15 | 16 | 17 | Residue | Loss | Calculated[2] Composite |
|---|---|---|---|---|---|---|---|---|
| Distillation Temperature (° C) | 160 | 164 | 170 | 176 | 207 | | | |
| Sample Weight (g) | 51.0 | 19.3 | 15.4 | 55.0 | 35.0 | 38.1 | 34.3 | |
| | GC ANALYSES, AREA PERCENT | | | | | | | |
| Unknowns | | | | | | | | 0.1 |
| m-Cresol | | | trace | | | | | 9.6 |
| Unknowns | | | | | | | | 3.6 |
| Thymol | | 0.1 | 0.1 | | | | | 18.8 |
| 5-Isopropyl-m-Cresol | 87.0 | 38.6 | 5.5 | | | | | 39.2 |
| 4-Isopropyl-m-Cresol | 7.2 | 32.9 | 14.5 | | | | | 2.6 |
| Unknowns | 5.8 | 26.2 | 60.3 | 11.6 | 2.7 | | | 5.3 |
| 4,6-Di-isopropyl-m-Cresol | — | 2.0 | 18.4 | 59.0 | 38.2 | | | 10.5 |
| Unknowns | — | | 1.2 | 29.4 | 59.1 | | | 10.2 |

[1] Fraction Cut - 17 was flash distilled from the residue to 207° at 6 mm Hg
[2] Calculated from the weights of distillates, and the GC analyses of all fractions

EXAMPLE 2

The procedure described in Example 1 was repeated except the isomerization was performed during eight hours at a temperature of about 300°–305° C. The results are shown in Table 3:

TABLE 3

5-Isopropyl-m-Cresol by Isopropylation of m-Cresol

| Sample 3520-233- | 1[1] | 6[2] |
|---|---|---|
| | GC Analyses Area Percent | |
| Unknowns | 0.4 | 0.8 |
| m-Cresol | 9.0 | 9.9 |
| Unknowns | 1.6 | 6.6 |
| Thymol | 30.7 | 19.8 |
| 5-Isopropyl-m-cresol | 23.4 | 42.4 |
| 4-Isopropyl-m-cresol | 5.0 | 2.1 |
| Unknowns | 3.6 | 5.9 |
| 4-6 Diisopropyl-m-cresol | 22.3 | 5.8 |

TABLE 3-continued

| 5-Isopropyl-m-Cresol by Isopropylation of m-Cresol | | |
|---|---|---|
| Unknowns | 4.0 | 6.6 |

[1]End of addition sample
[2]End of Isomerization sample

EXAMPLE 3

An alkylation-isomerization procedure similar to that described in Example 1 was repeated with the following changes. The catalyst was 5% by weight of a rare earth type "Y" mol sieve catalyst (Linde SK-500) which was ground up to pass a No. 40 standard screen. The final alkylation temperature was only about 225° C compared to final alkylation temperatures of greater than 250° C for examples 1 and 2. However isomerization at 280° C gave a product containing very favorable ratios of m-thymol to the other isopropylated m-cresols. The isomerization step was completed more rapidly using the mole sieve catalyst. The results are illustrated in Table 4:

TABLE 4

5-Isopropyl-m-cresol by Isopropylation of m-Cresol

| | 1[1] | 2[2] | 3[3] | Product[4] |
|---|---|---|---|---|
| | GC Analyses | | | Area Percent |
| Unknowns | 0.5 | 1.7 | 1.6 | 5.7 |
| m-Cresol | 15.5 | 11.3 | 11.5 | 11.7 |
| Unknowns | 0.3 | 10.5 | 11.3 | 11.1 |
| Thymol | 28.0 | 11.6 | 10.6 | 10.0 |
| 5-Isopropyl-m-cresol | 4.0 | 49.5 | 50.7 | 50.0 |
| 4-Isopropyl-m-cresol | 14.2 | 1.4 | 1.1 | 0.6 |
| Unknowns | 3.8 | 7.0 | 7.1 | 6.3 |
| 4,6 Di-isopropyl-m-cresol | 32.5 | 3.4 | 2.5 | 1.6 |
| Unknowns | 1.0 | 3.6 | 3.6 | 3.0 |

[1]End of addition sample
[2]Two hour isomerization sample
[3]Four hour isomerization sample
[4]End of 11 hr. isomerization sample

EXAMPLE 4

A series of experiments were performed in an attempt to make a purer product. This problem was difficult because the more severe conditions required to give a high ratio of m-thymol to p-thymol enhanced the production of other impurities, particularly the 2,4- and 2,5- diisopropyl phenols which boil right with the desired m-thymol. A high ratio of m-thymol to p-thymol is necessary because of the close boiling temperatures of these two isomers. However, a very low concentration of the di-isopropylated phenols is also necessary in order that pure m-thymol may be obtained. Mild isomerization conditions which give low concentrations of the close boiling di-isopropylated compounds also give low ratios of m-thymol to p-thymol. I have found that lowering the ratio of propylene to m-cresol minimizes the concentration of the di-isopropylated phenols and cresols but still allows good ratios of m-thymol to p-thymol.

The alkylation-isomerization procedure described in Example 1 was repeated with the following changes. The mole ratio of propylene to m-cresol was 0.87:1.0. The isomerization temperature was 200° C and the catalyst was 5% Filtrol 13. The isomerization reaction was run for 32 hours at about 200° C. At the end of 32 hours the reaction product contained very unfavorable ratios of the desired product. The ratio of m-thymol to p-thymol was about 5:11 and the ratio of m-thymol to di-isopropylated cresols was about 5:18. From these results it can be seen that it is necessary to run the isomerization reaction at higher temperatures as mentioned supra.

EXAMPLE 5

Another alkylation-isomerization reaction was run. The ratio of propylene to m-cresol was 0.73:1.0. The catalyst was 5% SK-500 and the isomerization was run at 275° C for about three hours. The reaction product contained favorable ratios. The ratio of m-thymol to thymol was 42:10. The ratio of m-thymol to p-thymol was about 42:3 and the ratio of m-thymol to di-isopropylated compounds was about 42:1.

EXAMPLE 6

Another alkylation-isomerization reaction was run in a manner similar to Example 1. The catalyst was 5% SK-500. The ratio of propylene to m-cresol was 0.5:1. The isomerization was run at a temperature of about 277° C for about four hours. At the end of four hours the reaction product contained the following ratios of desired product. The ratio of m-thymol to thymol was about 33:7. The ratio of m-thymol to p-thymol was about 33:2. The ratio of m-thymol to vic-thymol was about 33:1 and the ratio of m-thymol to di-isopropylated m-cresols was about 33:0.5.

EXAMPLE 7

Another alkylation-isomerization reaction was run in a manner similar to Example 1. The catalyst was 1% SK-500. The ratio of propylene to m-cresol was about 0.48:1. The isomerization was run at a temperature of about 275° C for about 5 hours. At the end of the isomerization the reaction product contained the following ratio of desired product. The ratio of m-thymol to thymol was about 33:12. The ratio of m-thymol to p-thymol was about 33:3. The ratio of m-thymol to vic-thymol was about 33:5 and the ratio of m-thymol to di-isopropylated m-cresols was about 33:1.0.

EXAMPLE 8

Another alkylation-isomerization was run in a manner similar to Example 1. The catalyst was 0.5% SK-500. The ratio of propylene to m-cresol was 0.55:1. The isomerization was run at a temperature of about 282° C for about 6.5 hours. At the end of the isomerization reaction the reaction product contained the following ratio of desired products. The ratio of m-thymol to thymol was about 27:18. The ratio of m-thymol to p-thymol was about 27:4.5 and the ratio of m-thymol to di-isopropylated m-cresol was about 27:2. From Examples 7 and 8 it can be seen that a catalyst concentration of about 1.0% is necessary in order to obtain a reasonable isomerization rate and sufficiently favorable ratios of m-thymol to other products.

EXAMPLE 9 sec-Butylation of m-Cresol

A 1-liter Parr autoclave was charged with 528.0 g (4.9 moles) of m-cresol and 13 g (2.5% based on m-cresol) of powdered SK-500, Linde's rare earth-exchanged type Y molecular sieve.

The temperature was raised to 175° C and 138.9 g (2.48 moles) of 1-butene was added during 80 min. while the reaction mixture was stirred at 175°–180° C. A sample was withdrawn at the end of the alkylation period and analysis by G. C. showed the composition listed in Table 5.

The temperature of the reaction mixture was raised and the product was stirred at 244°–250° C during 10.7 hours. A sample of the isomerized product showed the composition given in Table 5 by G. C. analysis.

TABLE 5

G.C. Analysis of Samples from Example 9

| Component | After Alkylation | After Isomerization |
|---|---|---|
| m-cresol | 44.5 | 41.4 |
| 6-sec-Butyl-m-cresol | 33.1 | 12.4 |
| 5-sec-Buty-m-cresol | 0.0 | 46.2 |
| 4-sec-Butyl-m-cresol | 16.2 | 0.0 |
| 2,6-Di-sec-butyl-m-cresol | 1.9 | 0.0 |
| 4,6-Di-sec-butyl-m-cresol | 4.4 | 0.0 |

15 ft. × ¼ in. DEPC-Black Sealing Wax; 190° C, 75 ml. He/min.

EXAMPLE 10 sec-Butylation of m-Cresol

A 2-liter Parr autoclave was charged with 1081.3 g (10 moles) of m-cresol and 32.4 g (3% based on m-cresol) of powdered SK-500, Linde's rare earth exchanged type Y molecular sieve.

The temperature was raised to 175° C and 359 g (6.4 moles) of 1-butene was added during 1.1 hrs. while the reaction mixture was stirred at 175°–193° C. A sample was withdrawn at the end of the alkylation period and analyzed by G. C. The results are listed in Table 6.

The product was then stirred at 260° C for 17.3 hrs. The composition of the isomerized product is given in Table 6.

TABLE 6

G.C. Analysis of Samples from Example 10

| Component | After Alkylation | After Isomerization |
|---|---|---|
| m-Cresol | 34.4 | 29.3 |
| 6-sec-Butyl-m-cresol | 38.4 | 14.9 |
| 5-sec-Butyl-m-cresol | 0.0 | 55.8 |
| 4-sec-Butyl-m-cresol | 17.8 | 0.0 |
| 2,6-Di-sec-butyl-m-cresol | 2.0 | 0.0 |
| 4,6-Di-sec-butyl-m-cresol | 7.5 | 0.0 |

15 ft. × ¼ in. DEPC-Black Sealing Wax; 190° C, 75 ml. He/min.

EXAMPLE 11

Isopropylation of m-Cresol

A 1-liter Parr autoclave was charged with 528.0 (4.9 moles) of m-cresol and 13g (2.5% based on m-cresol) of powdered SK-500, Linde's rare earth-exchanged type Y molecular sieve. During 0.4 hr. 105.9 g (2.52 moles) of propylene was added with stirring at 180°–240° C. A sample was taken at the end of alkylation and analyzed by G. C. The components are listed in Table 7.

The temperature was then raised and the reaction mixture was stirred at 260°–265° C for 20 hrs. A sample of the product was analyzed by G. C. to give the composition shown in Table 7.

TABLE 7

G.C. Analysis of Samples from Example 11

| Component | After Alkylation | After Isomerization |
|---|---|---|
| m-Cresol | 76.9 | 45.2 |
| 6-Isopropyl-m-cresol | 16.9 | 7.5 |
| 5-Isopropyl-m-cresol | 0.0 | 45.7 |
| 2,6-Di-isopropyl-m-cresol | 3.9 | 0.0 |

TABLE 7-continued

G.C. Analysis of Samples from Example 11

| Component | After Alkylation | After Isomerization |
|---|---|---|
| 4,6-Di-isopropyl-m-cresol | 2.3 | 0.0 |
| Unknown | 0.0 | 1.6 |

1. 15. × ¼ in. DEPC-Black Sealing Wax; 190° C, 75 ml. He/min.

EXAMPLE 12

Reaction of m-Cresol with Cyclohexene

A 1-liter Parr autoclave was charged with 528.0 g (4.9 moles) of m-cresol, 13 g (2.5% based on m-cresol) of powdered SK-500, Linde's rare earth-exchanged type Y molecular sieve, and 197.2 g (2.4 moles) of cyclohexene.

Temperature of the reaction mixture was raised to 160° C over 1.6 hrs. and the latter was stirred at 160°–167° C for 1.3 hrs. A sample was withdrawn and analyzed by G. C. The distribution of products is shown in Table 8.

The temperature was then raised to 260° C and the reaction mixture stirred for 12.2. hrs. A sample of the product was analyzed by G. C. The final distribution of components is shown in Table 8. The 5-cyclohexyl-m-cresol was identified by ir and nmr. This compound is useful as an intermediate in the preparation of insecticides and drugs. In addition it is useful in the preparation of polymeric resins. The m-cyclohexyl group imparts novel properties to the resins.

TABLE 8

G.C. Analysis of Samples from Example 12

| Component | After Alkylation | After Isomerization |
|---|---|---|
| m-Cresol | 68.3 | 55.1 |
| 6-Cyclohexyl-m-cresol | 11.0 | 8.5 |
| 5-Cyclohexyl-m-cresol | 0.0 | 27.3 |
| 4-Cyclohexyl-m-cresol | 5.2 | 0.0 |
| Unknown* | 15.5 | 5.8 |

15 ft. × ¼ in. DEPC-Black Sealing Wax; 220° C, 75 ml. He/min.

*Eluting after 4-cyclohexyl-m-cresol.

EXAMPLE 13

Reaction of m-Cresol with Cyclohexene

A catalyst was prepared by heating type Y ammonium ion molecular sieve in a tube furnace with a nitrogen sparge at 360°–400° C until ammonia ceased to evolve. An 11.6 g sample of the modified catalyst, 528.0 g (4.9 moles) of m-cresol and 197.2 g (2.5 moles) of cyclohexene were charged to a 1-liter Parr autoclave.

The temperature was raised to 165° C in one hour and a sample was withdrawn. G. C. analysis of the sample is shown in Table 9. (Sample 1)

The mixture was further alkylated and isomerized at 260° for 10 hrs. A sample was analyzed with the results shown in Table 9.

Further isomerization at 300° for 5 hours gave the results included in Table 9 (Sample 3).

TABLE 9

G.C. Analysis of Samples from Example 13

| Component | Sample 1 | Sample 2 | Sample 3 |
|---|---|---|---|
| Cyclohexene | 18.03 | — | — |
| m-Cresol | 66.57 | 47.42 | 61.01 |

TABLE 9-continued

G.C. Analysis of Samples from Example 13

| Component | Area Percent | | |
|---|---|---|---|
| | Sample 1 | Sample 2 | Sample 3 |
| m-Tolyl cyclohexyl ether | 3.45 | | |
| Intermediates* | — | 7.37 | 10.07 |
| 2-Cyclohexyl-m-cresol | 1.71 | | |
| 6-Cyclohexyl-m-cresol | 5.50 | 23.30 | 5.65 |
| 5-Cyclohexyl-m-cresol | — | 21.87 | 23.25 |
| 4-Cyclohexyl-m-cresol | 4.81 | — | — |

15 ft. × ¼ in. DEPC-Black Sealing Wax; 220° V, 76 ml. He/min.

*Tentatively identified as mixed cyclohexyl-o-cresols.

EXAMPLE 14

Reaction of m-Cresol with Styrene

A 1-liter Parr autoclave was charged with 528 (4.9 moles) of m-cresol, 249.7 g (2.4 moles) of styrene and 15.8 g (5% based on m-cresol) of powdered SK-500, Linde's rare earth-exchange Type Y molecular sieve. The alkylation was performed at 167°–192° during 1.4 hrs. with stirring, followed by a 2.5 hr. isomerization period at 275°. The reaction mixture was flash distilled at 25 mm Hg and the last fraction, which was mostly solid, was filtered. A recrystallization from hexane-benzene gave a white solid of melting point 120.5°–133° which was identified as 5-($\alpha$-methylbenzyl)-m-cresol by infrared spectroscopy and nmr spectroscopy. This compound is useful as an intermediate in the preparation of drugs and insecticides. It is also useful in polymeric resins.

EXAMPLE 15

Simultaneous Preparation of Thymol and m-Thymol

This example demonstrates a method of obtaining high conversions of thymol and 5-thymol.

An alkylation similar to that described in Example 1 was performed and the Filtrol 13 catalyst concentration was again 5% based on m-cresol and the final molar ratio of propylene to m-cresol was 0.87. The maximum alkylation temperature was 172° and the pressure was 45 psig. A sample was withdrawn at the end of the alkylation period and showed 19.3% m-cresol, less than 0.1% vic-thymol, 41.7% thymol, 1.7% m-thymol, 12.6% thymol, 6.0% 2,6-disopropyl-m-cresol, and 15.0% of 4,6-isomer and small concentration of other components.

The reaction product, still containing the catalyst, was removed from the pressure vessel and fractionally distilled at 20 mm Hg. Three fractions, the first, m-cresol, boiling at 90°–103°, the second, boiling at 103°–120° and composed of m-cresol and 2- and 6-thymol and the third boiling at 120°–125° and composed of relatively pure thymol, were isolated. The distillation was halted, and Fractions 1 and 2 were combined with the residue and the mixture was isomized and trans-alkylated in the autoclave for 6 hours at 280°. The product showed 25.3% m-cresol, 1.1% 2-thymol, 10.7% thymol, 42.3% 5-thymol, 3.2% 4-thymol, and small concentrations of other components. The product was filtered and the 5-thymol was isolated by fractionation.

What is claimed is:

1. A method for preparing 5 sec-alkyl-m-eresols in high concentrations comprising:
   a. alkylating m-cresol with an alkene at a temperature of at least about 100° C. over a catalyst selected from silica-alumina clays and molecular sieves to form a mixture of alklated m-cresol products; and
   b. isomerizing the alkylated mixture over the same catalyst for at least about two hours at a temperature of from about 250° C. to 400° C.

2. A method as in claim 1 wherein the molar ratio of alkene to m-cresol is from about 0.5:1 to about 1.0:1.0.

3. A method as in claim 1 wherein the catalyst is from about 1.0% to about 10.0% by weight based on m-cresol.

4. A method as in claim 1 wherein the isomerization is run for about 2 to 12 hours at a temperature from about 250° to 400° C.

5. A method for preparing 5 sec-alkyl-m-cresols in high concentrations comprising:
   a. alkylating m-cresol with an alkene at a temperature of at least about 100° C over a catalyst selected from finely divided silica-alumina clays and finely divided molecular sieves to form a mixture of alkylated m-cresol products wherein the molar ratio of alkene to m-cresol is from about 0.5:1.0 to about 1.0:1.0; and
   b. isomerizing the alkylated mixture over the same catalyst for about 2 to 12 hours at a temperature from about 250° to 400° C and wherein the catalyst is from about 1.0% to about 10.0% by weight based on m-cresol.

6. A method for preparing 5 sec-alkyl-m-cresols in high concentrations comprising:
   a. alkylating m-cresol with an alkene at a temperature of at least about 100° C. over a catalyst selected from finely divided silica-alumina clays and finely divided molecular sieves of the faujasite type to form a mixture of alkylated m-cresol products wherein the molar ratio of the alkene to m-cresol is from about 0.5:1.0 to about 1.0:1.0; and
   b. isomerizing the alkylated mixture over the same catalyst for at least about two hours at a temperature of from about 250° C. to 400° C. wherein the catalyst is from about 1.0% to about 10.0% by weight based on m-cresol;
   c. fractionally distilling the isomerized alkylated mixture to obtain the 5 sec-alkyl-m-cresol.

7. A method as in claim 6 wherein the isomerization is run for about 2 to 12 hours at a temperature of from about 250° C to about 400° C.

8. A method for preparing 5 sec-alkyl-m-cresols in high concentrations comprising:
   a. alkylating m-cresol with an alkene at a temperature of at least about 100° C. over a catalyst selected from finely divided silica-alumina clays and finely divided molecular sieves of the faujasite type to form a mixture of alkylated m-cresol products wherein the molar ratio of alkene to m-cresol is from about 0.5:1.0 to about 1.0:1.0; and
   b. isomerizing the alkylated mixture over the same catalyst for about two hours at a temperature of from about 250° C. to 400° C. wherein the catalyst is from about 1.0% to about 10.0% by weight based on m-cresol;
   c. fractionally distilling the isomerized alkylated mixture to obtain the 5 sec-alkyl-m-cresol;
   d. recycling the undesired alkylated products.

9. A method as in claim 8 wherein the unreacted m-cresol is recycled to the alkylating step.

10. A method for preparing 5 sec-alkyl-m-cresol in high concentrations comprising:

a. alkylating m-cresol with an alkene at a temperature of at least about 100° C. over a catalyst selected from silica-alumina clays and molecular sieves of the faujasite type to form a mixture of alkylated m-cresol products wherein the molar ratio of alkene to m-cresol is from about 0.5:1.0 to about 1.0:1.0; and b. isomerizing the alkylated mixture over the same catalyst for at least about two hours at a temperature of from about 250° C. to 400° C. wherein the catalyst is from about 1.0 to about 10.0% by weight based on the m-cresols, alkylated and unalkylated;

c. fractionally distilling the isomerized alkylated mixture to obtain the 5 sec-alkyl-m-cresol;

d. recycling the unreacted m-cresol to the alkylation step and the 6-isomer, 4-isomer, 2-isomer, di-alkylated m-cresols and other undesired alkylated products to the isomerization step.

11. A method as in claim 10 wherein the 6-isomer, 4-isomer, 2-isomer, di-alkylated m-cresols and other undesired alkylations products are recycled to the isomerization step and the unreacted m-cresol is recycled to the alkylation step.

12. A method as in claim 10 wherein cuts from the fractional distillation step which contain substantial amounts of 5-sec-alkyl-m-cresol are recycled to the fractional distillation step.

13. A method for preparing m-thymol in high concentrations comprising:

a. isopropylating m-cresol with propylene at a temperature of at least about 100° C. over a catalyst selected from silica-alumina clays and molecular sieves of the faujasite type to form a mixture of isopropylated m-cresol products; and b. isomerizing the isopropylated mixture over the same catalyst for at least about 2 hours at a temperature of from about 250° C. to 400° C.

14. A method as in claim 13 wherein the molar ratio of propylene to m-cresol is from about 0.5:1 to about 1.0:1.0.

15. A method as in claim 13 wherein the catalyst is from about 1.0% to about 10.0% by weight based on m-cresol.

16. A method as in claim 13 wherein the isomerization is run for about 2 to 12 hours at a temperature from about 250° to 400° C.

17. A method for preparing m-thymol in high concentrations comprising:

a. isopropylating m-cresol with propylene at a temperature of at least about 100° C over a catalyst selected from finely divided silica-alumina clays and finely divided molecular sieves of the faujasite type to form a mixture of isopropylated m-cresol products wherein the molar ratio of propylene to m-cresol is from about 0.5:1.0 to about 1.0:1.0; and b. isomerizing the isopropylated mixture over the same catalyst for about two to twelve hours at a temperature from about 250° to 400° C and wherein the catalyst is from about 1.0% to about 10.0% by weight based on m-cresol.

18. A method for preparing m-thymol in high concentrations comprising:

a. isopropylating m-cresol with propylene at a temperature of at least about 100° C. over a catalyst selected from finely divided silica-alumina clays and finely divided molecular sieves of the faujasite type to form a mixture of isopropylated m-cresol products wherein the molar ratio of propylene to m-cresol is from about 0.5:1.0 to about 1.0:1.0; and b. isomerizing the isopropylated mixture over the same catalyst for at least about two hours at a temperature of from about 250° c. to 400° C. wherein the catalyst is from about 1.0% to about 10.0% by weight based on m-cresol;

c. fractionally distilling the isomerized isopropylated mixture to obtain the m-thymol.

19. A method as in claim 10 wherein the isomerization is run for about 2 to 12 hours at a temperature of from about 250° C to about 400° C.

20. A method for preparing m-thymol in high concentrations comprising:

a. isopropylating m-cresol with propylene at a temperature of at least about 100° C. over a catalyst selected from finely divided silica-alumina clays and finely divided molecular sieves of the faujasite type to form a mixture of isopropylated m-cresol products wherein the molar ratio of propylene to m-cresol is from about 0.5:1.0 to about 1.0:1.0; and b. isomerizing the isopropylated mixture over the same catalyst for at least about 2 hours at a temperature of from about 250° C to 400° C. wherein the catalyst is from about 1.0% to about 10.0% by weight based on m-cresol;

c. fractionally distilling the isomerized isopropylated mixture to obtain the m-thymol;

d. recycling the undesired isopropylated products.

21. A method as in claim 20 wherein the unreacted m-cresol is recycled to the isopropylating step.

22. A method as in claim 20 wherein the m-cresol and thymol, p-thymol, vic-thymol, di-isopropylated m-cresols and other undesired isopropylation products are recycled to the isopropylating step.

23. A method as in claim 20 wherein the thymol, p-thymol, vic-thymol, di-isopropylated m-cresols and other undesired isopropylation products are recycled to the isomerization step and the m-cresol is recycled to the isopropylating step.

24. A method as in claim 20 wherein cuts from the fractional distillation step which contain substantial amounts of m-thymol are recycled to the fractional distillation step.

25. A method for preparing m-thymol in high concentrations comprising:

a. isopropylating m-cresol with propylene at a temperature of at least about 200° C. over a catalyst selected from finely divided silica-alumina clays and finely divided molecular sieves of the faujasite type to form a mixture of isopropylated m-cresol products wherein the molar ratio of propylene to m-cresol is from about 0.5:1.0 to about 1.0:1.0; and b. isomerizing the isopropylated mixture over the same catalyst for at least about 2 hours at a temperature of from about 250° C. to 400° C. wherein the catalyst is from 1.0 to about 10.0% by weight based on the m-cresols, isopropylated and unisopropylated;

c. fractionally distilling the isomerized isopropylated mixture to obtain the m-thymol;

d. recycling the unreacted m-cresol and thymol, p-thymol, victhymol, di-isopropylated m-cresols and other undesired isopropylated products to the isopropylating step.

26. A method as in claim 25 wherein the thymol, p-thymol, vic-thymol, di-isopropylated m-cresols and other undesired isopropylation products are recycled to the isomerization step and the unreacted m-cresol is recycled to the isopropylating step.

27. A method as in claim 25 wherein cuts from the fractional distillation step which contain substantial amounts of m-thymol are recycled to the fractional distillation step.

28. A method for simultaneously preparing thymol and m-thymol comprising:
   a. isopropylating m-cresol with propylene at a temperature of at least about 100° C. over a catalyst selected from finely divided silica-alumina clays and finely divided molecular sieves of the faujasite type to form a mixture of isopropylated m-cresol products wherein the molar ratio of propylene to m-cresol is from about 0.5:1.0 to about 1.0:1.0; and
   b. recovering the thymol by fraction distillation;
   c. combining the undesirable fractions and residue from the thymol fractional distillation and isomerizing this mixture for at least about 2 hours at a temperature of from about 250° C to 400° C. wherein the catalyst is from about 1.0 to about 10.0% by weight based on the m-cresols, isopropylated and unisopropylated;
   d. fractionally distilling the isomerized isopropylation mixture to obtain m-thymol.

29. A method as in claim 28 wherein the undesired isopropylated products are recycled to the isomerization step and the unreacted m-cresol is recycled to the isopropylating step.

30. The composition of matter of 5-cyclohexyl-m-cresol.

31. The composition of matter of 5-α-methylbenzyl-m-cresol.

* * * * *

UNITED STATES PATENT OFFICE
CERTIFICATE OF CORRECTION

PATENT NO. : 3,992,455
DATED : November 16, 1976
INVENTOR(S) : Gerd Leston

It is certified that error appears in the above—identified patent and that said Letters Patent are hereby corrected as shown below:

Claim 25 at column 16, line 50:

The temperature 200°C should be 100°C

Signed and Sealed this

Eighth Day of March 1977

[SEAL]

Attest:

RUTH C. MASON
Attesting Officer

C. MARSHALL DANN
Commissioner of Patents and Trademarks